(12) United States Patent
Whitmore

(10) Patent No.: US 8,951,547 B2
(45) Date of Patent: Feb. 10, 2015

(54) DRUG DELIVERY SYSTEM

(71) Applicant: Lumemed Limited, Prudhoe (GB)

(72) Inventor: Alan Whitmore, Dyrham (GB)

(73) Assignee: Lumemed Limited, Warden, Northumberland (GB)

( * ) Notice: Subject to any disclaimer, the term of this patent is extended or adjusted under 35 U.S.C. 154(b) by 0 days.

(21) Appl. No.: 13/939,528

(22) Filed: Jul. 11, 2013

(65) Prior Publication Data

US 2013/0296632 A1 Nov. 7, 2013

Related U.S. Application Data

(63) Continuation of application No. 12/162,180, filed as application No. PCT/GB2007/000187 on Jan. 22, 2007, now Pat. No. 8,486,440.

(30) Foreign Application Priority Data

Jan. 25, 2006 (GB) .................................. 0601502.8

(51) Int. Cl.
| | | |
|---|---|---|
| *A61F 9/00* | (2006.01) | |
| *A61N 2/10* | (2006.01) | |
| *A61N 5/01* | (2006.01) | |
| *A61K 9/14* | (2006.01) | |
| *A61N 2/00* | (2006.01) | |
| *A61K 9/00* | (2006.01) | |
| *A61N 2/06* | (2006.01) | |
| *A61K 41/00* | (2006.01) | |

(52) U.S. Cl.
CPC .............. *A61N 2/004* (2013.01); *A61K 9/0009* (2013.01); *A61N 2/06* (2013.01); *A61F 9/00* (2013.01); *A61K 41/00* (2013.01); *A61K 41/0042* (2013.01); *Y10S 977/906* (2013.01)
USPC .............. 424/427; 424/489; 600/12; 977/906

(58) Field of Classification Search
None
See application file for complete search history.

(56) References Cited

U.S. PATENT DOCUMENTS

| 8,486,440 B2 | 7/2013 | Whitmore |
| 2003/0191458 A1 | 10/2003 | Diamond et al. |
| 2004/0166553 A1 | 8/2004 | Nguyen et al. |
| 2008/0213177 A1 * | 9/2008 | Rademacher et al. ....... 424/1.73 |

FOREIGN PATENT DOCUMENTS

| WO | 01/51087 | 7/2001 |
| WO | 03066066 | 8/2003 |
| WO | 2005059158 | 6/2005 |
| WO | 2005110397 | 11/2005 |

OTHER PUBLICATIONS

Ottl, et al., Preparation and Photoactivation of Caged Fluorophores and Caged Proteins Using a New Class of Heterobifunctional, Photocleavable Cross-Linking Reagents, Bioconjugate Chemistry, vol. 9 No. 2, 143-51 (1998).*
Stacy et al., "Radiation-guided drug delivery systems", Expert Rev. Anticancer Ther., Apr. 2004, vol. 4, No. 2, pp. 283-288.
Ottl et al., Preparation and Photoactivation of Caged Fluorophores and Caged Proteins Using a New Class of Heterobifunctional, Photocleavable Cross-Linking Reagents, Bioconjugate Chemistry, 1998, vol. 9, No. 2, pp. 143-151.
International Search Report, PCT/GB2007/000187, dated Apr. 27, 2007, 4 pages.
Written Opinion, PCT/GB2007/000187, dated Apr. 27, 2007, 7 pages.
International Preliminary Report on Patentability, PCT/GB2007/000187, dated Apr. 27, 2007, 7 pages.

* cited by examiner

*Primary Examiner* — H. Sarah Park
(74) *Attorney, Agent, or Firm* — Senniger Powers LLP

(57) ABSTRACT

An ocular drug delivery system comprising a photocaged drug comprising a therapeutic agent that is rendered biologically inactive by being coupled to a protective ligand or caging group by a photocleavable bond, with the therapeutic agent being capable of being activated and/or released in response to a predetermined wavelength and/or intensity of light which breaks the photocleavable bond.

9 Claims, 1 Drawing Sheet

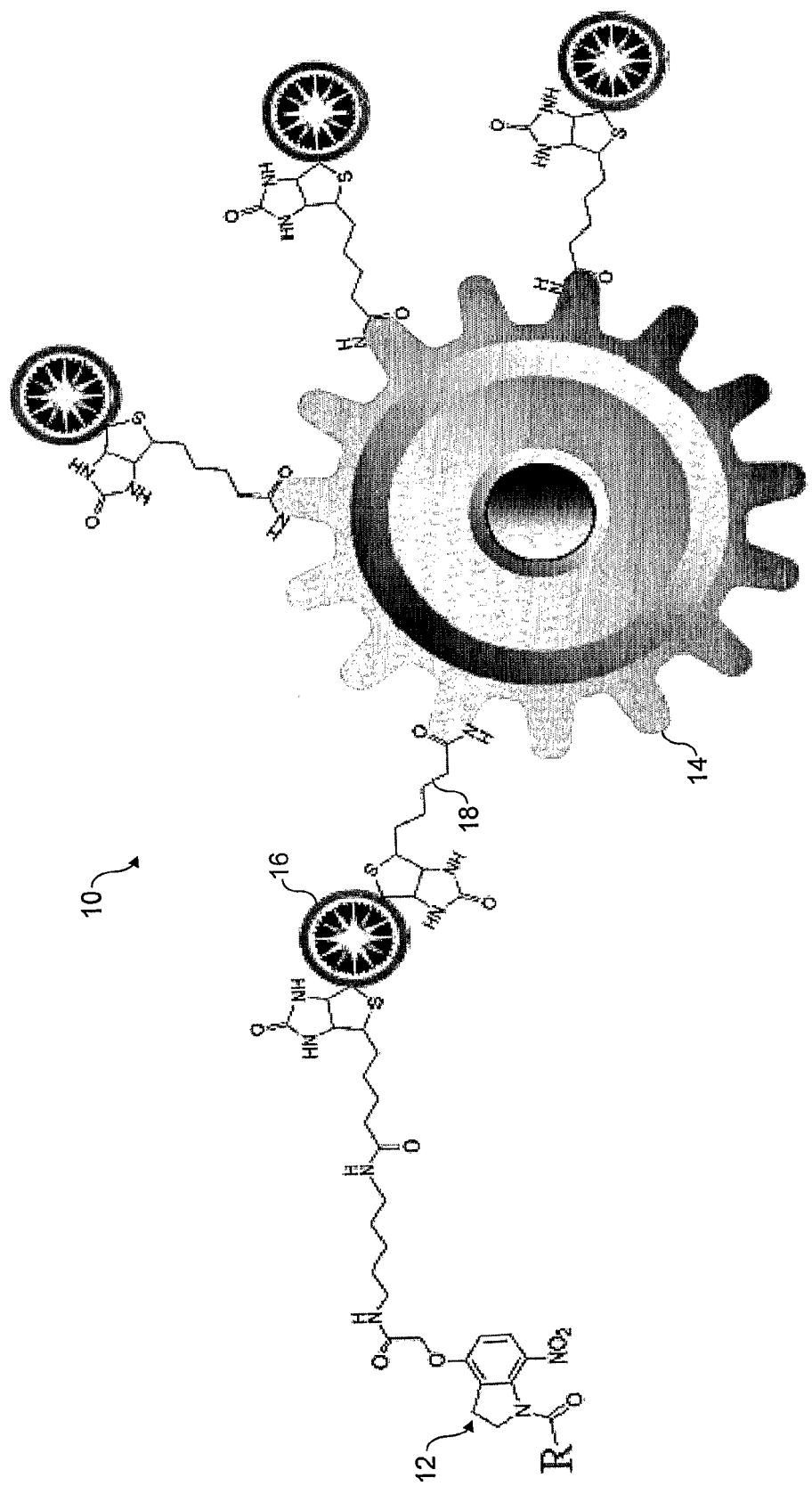

DRUG DELIVERY SYSTEM

REFERENCE TO RELATED APPLICATION

This is a continuation application of U.S. application Ser. No. 12/162,180, filed Aug. 6, 2008, and issued Jul. 16, 2013 as U.S. Pat. No. 8,486,440, which is a U.S. National Application of International Application No. PCT/GB07/00187, filed Jan. 22, 2007 and claims the benefit of Great Britain Application No. 0601502.8, filed Jan. 25, 2006, the entire disclosures of which are incorporated herein by reference.

FIELD OF THE INVENTION

The present invention relates to a drug delivery system. In particular, although not exclusively, the present invention relates to an intraocular drug delivery system.

BACKGROUND OF THE INVENTION

Various methods for intraocular drug delivery are known. For example, drugs may be administered topically by introducing eye drops into the eye. Generally, however, topical administration is only effective for treating conditions on the surface of the eye and to a lesser extent the anterior segment of the eye; it is difficult to deliver drugs in therapeutic concentrations beyond the cornea.

Intraocular injections have also been used to deliver drugs to the inside of the eye at therapeutic concentrations. However, such invasive methods of drug delivery require great technical skill and are extremely unpleasant for the patient. There is also the risk of infection, inflammation, hypotony, choroidal detachment, retinal detachment and haemorrhage with their consequent complications (that may in themselves lead to blindness).

To avoid injecting drugs directly into the eye, drugs may be administered by enteral (for example orally) or other parenteral routes (for example intravenously) and these may reach the eye via the circulation. Generally, however, these drugs have to be administered at high concentrations, since the active compound may be diluted by intravascular and extravascular fluids. This gives rise to a risk of toxicity to other organ systems and tissues. If lower concentrations are used to avoid toxicity and other side effects there is more risk of treatment failure, for example, due to the inactivation and/or excretion of the active compound by the liver and kidneys before it reaches the eye, particularly if the compound cycles repeatedly through these organs.

WO 01/51087 describes a method for treating neovascular diseases of the eye using photodynamic therapy (PDT). In PDT, a photosensitive compound is administered to the patient systemically or topically. The photosensitive compound has a characteristic light absorption spectrum and, when exposed to light within that waveband, produces reactive species, such as singlet oxygen atoms, which damage the surrounding cells. In the method of WO 01/51087, the photosensitizing compound is conjugated to, for example, antibodies and antibody fragments that are capable of targeting the complex by binding to the endothelium that lines the neovascular tissue. Once bound to the endothelium in this way the conjugated photosensitizing compound may be activated to cause damage to the targeted endothelial cells.

The aim of PDT is very specific and its effects are narrow. Its aim is to kill target tissues to achieve the intended therapeutic effect, rather than to deliver a therapeutic agent whose beneficial effects might be achieved by diverse and/or multiple means (and not necessarily by toxicity to diseased tissue). A further disadvantage of PDT is that the reactive species produced upon activation of the photosensitizing compound tend to act indiscriminately on the surrounding (non-diseased) tissue. This form of therapy, therefore, may only be suitable for treating specific conditions, where damage to surrounding tissue can be tolerated and where destruction of a target tissue is the desired outcome. For other conditions, it may be preferable to deliver therapeutic drugs or agents to the target site whose effect is not necessarily to kill target tissues or cells. Rather, as well as being capable of destroying target tissues and cells, such agents might also be designed to inhibit a biochemical process (such as inflammation), to suppress infection (e.g. antibiotics and antiviral agents), to act as an agonist or antagonist of an endogenous agent (such as Vasoactive Endothelial Growth Factor (VEGF)), or to modulate an endogenous pathway in some other way.

SUMMARY OF THE INVENTION

According to the present invention, there is provided a drug delivery system comprising a caged drug coupled to a magnetic moiety, wherein the drug is capable of being activated and/or released in response to a predetermined wavelength and/or intensity of radiation.

According to a further aspect of the invention, the present invention provides the use of the above system in a method for drug delivery, said method comprising administering the system to the patient, localising the system at the target site by the application of a magnetic field, and directing a predetermined wavelength and/or intensity of radiation to the target site to activate and release the caged drug at the target site.

BRIEF DESCRIPTION OF THE FIGURE

FIG. 1 is a schematic diagram of an embodiment of the system of the present invention.

DETAILED DESCRIPTION OF PREFERRED EMBODIMENTS

In the present application, the term "radiation" includes anything propagated as rays, waves or a stream of particles. Preferred forms of radiation include electromagnetic radiation and sound waves. Examples of suitable electromagnetic radiation include light in the infra-red, visible and/or ultraviolet range. Examples of suitable sound waves include audible sound and ultrasound.

Preferably, the magnetic moiety is a magnetic nanoparticle.

As will be explained in further detail below, the system of the present invention may be administered to a patient enterally or parenterally. The system may also be administered topically, for example, by inhalation or eyedrops. A magnetic field may then be used to localise the system at the target site for treatment. Radiation may then be directed to the target site to activate and release the caged drug at the desired location. Any form of radiation may be used. Examples include electromagnetic radiation, such as light, and sound radiation, such as ultrasound. Preferably, electromagnetic radiation, such as light (e.g. laser light) is employed.

The system of the present invention is especially suitable for treating transparent and/or semi-transparent tissue, as an external source of radiation, such as light, may be used to activate and/or release the caged drug. In a preferred embodiment of the invention, the system is used to administer drugs to the eye. A predetermined wavelength and/or intensity of radiation (e.g. light) may be shone into the eye to activate and/or release the caged drug at the target site.

The system of the present invention includes a caged drug. The caged drug comprises a therapeutic agent that is rendered biologically inactive by a protective ligand or caging group. Where the caged drug is one that is capable of being activated by a predetermined wavelength and/or intensity of electromagnetic radiation (e.g. light), the caged drug is termed a photocaged drug. Typically, the therapeutic agent is coupled to the ligand or caging group by a cleavable (e.g. photocleavable) bond. When illuminated by an appropriate wavelength and/or intensity of radiation, such as light, the cleavable bond breaks. This may release the therapeutic agent from the protective ligand or caging group. Alternatively or additionally, the cleavable (e.g. photocleavable) bond may break to unmask the therapeutic effect of the therapeutic agent by activating an active site or sites. Once released and/or activated, the therapeutic agent has its usual therapeutic activity.

The caged (e.g. photocaged) drug may include any suitable therapeutic agent. Suitable examples include but are not limited to macromolecules, such as antibodies and aptamers. Such macromolecules bind disease-causing molecules such as VEGF (in neovascular disease, for example, of the eye) and TNF (in the arthritides, for example, to treat the associated uveitis in the eye). Other examples of therapeutic agents include antisense DNA, RNA or siRNA. Such agents are intended to inhibit the expression of a gene and thereby modify the disease (for example, by suppression of the action of a constitutively active mutant protein such as guanylate cyclase as in some forms of retinitis pigmentosa, or to suppress a protein (for example guanylate cyclase) that is no longer being antagonised because of a mutation in its antagonist (for example phosphodiesterase beta) as in some forms of retinitis pigmentosa). Further examples include, but are not limited to, antibiotics (e.g. to treat acute or refractory intraocular infection), antivirals, antifungals, steroids, non-steroidal anti-inflammatory agents, analgesics, drugs affecting intraocular pressure, statins and neuroprotectants.

The therapeutic agent may be coupled to any suitable caging group. Preferred caging groups are photosensitive caging groups. Suitable examples of photosensitive caging groups include but are not limited to: substituted (2-) nitrobenzyls, dimethoxy nitrobenzyls, nitroveratryloxycarbonyl, 2-(dimethylamino)-5-nitrophenyl, Bis(o-nitrophenyl)ethanediol, brominated hydroxyquinoline, coumarin-4-ylmethyl derivatives, 7-nitroindolines, benzophenones, aziridines, ruthenium(II) organic complexes. The caging group may also be a photolabile cross-linking group. Examples include but are not limited to those groups described above e.g alpha-methyl 2-nitrobenzyls containing amino, hydroxy, bromo and methylamino groups as well as 4-nitrophenoxycarbonyl activated OH and NH2 groups.

The caged (e.g. photocaged) drug is coupled to a magnetic moiety. The magnetic moiety is preferably a nanoparticle. Suitable nanoparticles are 1 to 1000 nm in size, preferably 20 to 300 nm in size, more preferably 50 to 200 nm in size. In one embodiment, the nanoparticle is approximately 70 to 100 nm in size. Such nanoparticles favour retention within the intravascular compartment.

The magnetic moiety (e.g. magnetic nanoparticle) may include a magnetic core formed from a material that is attracted by a magnetic field gradient. Iron and/or iron containing materials may be used. In one embodiment, the magnetic core is formed from iron oxide(s), such as magnetite and/or maghaemetite. The magnetic core may be ferromagnetic or paramagnetic. Preferably, the magnetic core is superparamagnetic. Superparamagnetic cores cease to be magnetic in the absence of an applied magnetic field. Accordingly, particles with such cores are less likely to clump together during use.

The magnetic core may be <1 nm to 1000 nm, preferably, though not exclusively, 5 to 20 nm in size.

The magnetic core may be provided with a coating, such as a biocompatible coating. Suitable coating materials include but are not limited to cyclodextrin and polyethylene glycol.

The coating may be functionalised to allow organic and/or inorganic moieties to be coupled to the coating by, for example, covalent and/or ionic bonds. In one embodiment, the caged (e.g. photocaged) drug may be coupled directly or indirectly to the coating, for example, via such bonds. Alternatively or additionally, the caged (e.g. photocaged) drug may be provided with a coating that selectively binds to the magnetic moiety (e.g. magnetic nanoparticle). In one embodiment, the caged (e.g. photocaged) drug is modified with surface functional groups that selectively adhere to the coating on the magnetic moiety (e.g. nanoparticle). For example, when the magnetic moiety (e.g. nanoparticle) is provided with a streptavidin coating, the caged (e.g. photocaged) drug may be provided with a biotin/biotin derived functional group or coating or partial coating which couples to the coating on the magnetic nanoparticle (and vice-versa).

It may be possible to couple the caged (e.g. photocaged) drug to the magnetic moiety (e.g. nanoparticle) via a linking agent. The linking agent may itself be a modified nanoparticle and may confer an additional function to the complex. The linking agent may be coated with a coating that selectively adheres to the magnetic moiety (e.g. nanoparticle). In one embodiment, the linking agent is coated with a coating that selectively adheres to the coating on the magnetic moiety (e.g. nanoparticle) and simultaneously to functional groups on the drug. For example, when the magnetic moiety (e.g. nanoparticle) is provided with a biotin/biotin derivative coating and the drug also carried biotin-derived functional groups, the linking agent may be provided with a coating of streptavidin, which couples to the coating on the magnetic nanoparticle and the functional groups on the drug. Alternatively, when the magnetic nanoparticle and/or drug are provided with a streptavidin coating, the linking agent may be provided with a coating or partial coating of biotin/biotin derivative, which couples to the coating on the magnetic nanoparticle and on the drug.

Alternatively or additionally, the coating on the linking agent may be functionalised to allow organic and/or inorganic moieties to be coupled to the coating more directly via, for example, covalent and/or ionic bonds. In one embodiment, the caged (e.g. photocaged) drug or therapeutic agent (for example a protein or RNA molecule) and the surface-modified magnetic moiety are both coupled to the linker coating via such bonds. The caged (e.g. photocaged) drug or therapeutic agent may carry specifically designed binding group(s) as part of their structure which permit such binding or such groups may already be part of their structure.

In one embodiment, the caged (e.g. photocaged) drug carries binding groups that selectively adhere to the coating on the linking agent. These binding groups may be present on a coating on the caged (e.g. photocaged drug). For example, the caged (e.g. photocaged) drug may be provided with a coating of streptavidin, which couples to a coating of biotin on the linking agent. Alternatively, the caged (e.g. photocaged) drug may be provided with a coating or partial coating of biotin which couples to a streptavidin coating on the linking agent, or biotin derivatives may be incorporated co-valently into the drug's structure.

The linking agent may be from 1 to 100 nm in size, preferably, 5 to 50 nm in size.

The system of the present invention may also include a marker, for example, to provide the drug administrator (e.g. physician or surgeon) with an indication of whether the system is at its target site. The marker may be a visible marker, such as a dye. The dye may be visible to the naked eye or may be visualised by suitable imaging equipment and, optionally, a camera. For certain applications, it may be appropriate to use a dye that is visible under certain forms of radiation, such as shortwave light, for example in the range of 400 to 490 nm; or longwave light, for example in the range 750 to 850 nm.

In one embodiment, the marker is a luminescent marker. The luminescent marker may emit light spontaneously. When the luminescence is spontaneous and driven by a chemical process (e.g. oxidation of luciferin catalysed by luciferase) the luminescence occurs continuously in the presence of suitable substrate. Alternatively the marker may fluoresce once activated with a predetermined wavelength and/or intensity of light. Thus, by directing a predetermined wavelength of light at the target location, the drug administrator can activate the luminescent marker and determine whether the system has reached its target location. When the luminescent marker is fluorescent, the luminescence ceases as soon as the source of activating light is removed. In contrast, when the luminescent marker is phosphorescent, the luminescence persists for a period of time after the activating light source is removed. Spontaneously luminescent, fluorescent and phosphorescent markers may be employed.

The intensity of the luminescence/colour of the marker may provide the administrator with an indication of the concentration of the system at the target location.

Examples of suitable markers that may be used in the system of the present invention include but are not limited to fluorescein, indocyanine green and quantum dots. Suitable quantum dots are described in US 2002/0127224.

Quantum dots are small molecular clusters having up to about a few hundred atoms. Quantum dots are therefore larger than individual atoms, but quantum dots generally behave in accordance with the principles of quantum mechanics that govern the behaviour of individual atoms. Because of this behaviour, quantum dots are sometimes also called "artificial atoms". Quantum dots have a size in the region of about 1 nm to about 20 nm and are typically only a few nanometers in size.

A quantum dot is typically composed of a semi-conductor material or materials, metal(s), or metal oxides exhibiting a certain bandgap energy. Although it is preferred that biocompatible light-emitting nanoparticles such as $TiO_2$ are used in the practice of the invention, nanoparticles that are not generally considered to be biocompatible may also be used. A variety of materials may be utilized for construction of nanoparticles, including but not limited to $TiO_2$, $Al_2O_3$, AgBr, CdSe, CdS, $CdS_xSe_{1-x}$, CuCl, $CdTe_xS_{1-x}$, ZnTe, Se, ZnS, GaN, InGaN, InP, CdS/HgS/CdS, and InAs/GaAs. Group II-VI, and Groups I-VII semiconductors as well as Group IV metals and alloys from quantum dots and other nanoparticles as described below when formed sufficiently small. A quantum dot may also be surrounded by a material or materials having wider bandgap energies (for example, ZnS-capped CdS), and especially may be surrounded by those materials that improve biocompatibility of the nanoparticles.

Quantum dots fluoresce when stimulated by light having a wavelength in which the energy of a photon is at least equal to the bandgap energy of the light-emitting material forming the quantum dot. Consequently, quantum dots absorb light of a first wavelength and emit light at a second wavelength that is longer than the first wavelength. The pump light supplied by e.g. a laser or light-emitting diode ("LED") array or other light source in which photons have an energy at least equal to the band-gap energy of the quantum dot is therefore absorbed by the quantum dot. The quantum dot re-emits energy in the form of light at a different wavelength and in a multidirectional fashion.

Because a quantum dot is so small and is thus governed by the rules of quantum mechanics, the size of the dot dictates the wavelength, and hence the colour, of its fluorescence. The larger the diameter or width of a given quantum dot, the longer the wavelength of light that the quantum dot emits. For example, the band gap of a CdSe quantum can be tuned from deep red (1.7 eV) to green (2.4 eV) by reducing the diameter of the quantum dot from 200 Å to 20 Å.

There are a number of methods of making quantum dots. The synthesis of small semiconductor clusters in trioctylphosphine oxide (TOPO) at 300° C. has been shown to yield highly fluorescent (quantum yields >50%) small particles of a number of semiconductor materials, such as CdSe, InP and InAs. Growth conditions such as the length of time of crystallization, concentration of a monomer, and temperature establish the size of the quantum dot and therefore the colour of the light emitted from the quantum dot. Such methods are discussed in the articles by M. Green and P. O'Brien, "Recent advances in the preparation of semiconductors as isolated nanometric particles; new routes to quantum dots," Chem. Commun., 1999, 2235-41 ("Green et al. article"). See also U.S. Pat. Nos. 5,909,670, 5,943,354, and 5,882,779.

The marker may be coupled to the magnetic moiety (e.g. nanoparticle) using any suitable method. For example, the marker may be provided with a coating, which may be functionalised both to render it biocompatible and to bond to the magnetic moiety (e.g. nanoparticle), for example, via ionic and/or covalent bonds. Alternatively or additionally, the marker may be provided with a coating that selectively adheres to the magnetic moiety (e.g. nanoparticle). In one embodiment, the marker is provided with a coating that selectively adheres to the coating on the magnetic moiety (e.g. nanoparticle). For example, when the magnetic moiety (e.g. nanoparticle) is provided with a biotin coating, the marker may be provided with a coating of streptavidin (and vice-versa).

As well as being coupled to the magnetic moiety (e.g. nanoparticle), the marker may also be linked to the photocaged drug. In this regard, the marker may act as a linking agent, as described above.

The system of the present invention may be administered to a patient using any suitable method. For example, the system may be administered enterally or parenterally. Topical forms of administration (e.g. inhalation, eyedrops) may also be used. As described above, a magnetic field gradient may be used to localise the system at the target site for treatment. Preferably, the source of the magnetic field is located outside the patient's body.

Typically, magnetic field strengths of the order of 1 Tesla ($10^4$ Gauss) will be employed. The magnetic field may be provided by any suitable magnet. For example, a neodymium magnet may be used.

The system of the present invention is particularly suitable for delivering drugs to transparent or semi-transparent tissue. For example, the system of the present invention may be used to deliver drugs to treatment sites at or just beneath the surface of the skin, or beneath the surface of the conjunctival covering of the eye. This allows the caged (photocaged) drug to be activated using an external source of radiation, such as light. Where, for example, a visible marker is used, this marker may be observed from the outside. Any luminescent marker may also be activated using an external source of radiation.

In a preferred embodiment of the present invention, the system of the present invention is used to deliver drugs to the eye. As the eye is substantially transparent (via the cornea and lens), the caged (photocaged) drug may be activated by directing an external source of radiation (e.g. light) into the eye. Any marker present in the system may also be visible from the outside. Similarly, any luminescent marker may also be activated using an external source of light.

Once the system of the present invention is localised, a predetermined wavelength and/or intensity of radiation (e.g. electromagnetic or sound) can be delivered to the target site to activate and/or release the caged (photocaged) drug at the target site. Any suitable type of radiation may be used. For example, sound, ultrasound, UV, visible light or near infrared light may be employed although, preferably, visible light will be employed to activate drugs either by the single photon or two/multiphoton technique. In the two/multi photon technique, two or more photons, which individually have insufficient energy to cause activation, interact co-operatively to achieve activation. The technique generally depends on two or more photons arriving in a very short space of time.

Suitable activating wavelengths could range from 300 to 1000 nm, preferably 400 to 800 nm, for example, 632 nm light from a HeNe laser.

Any suitable intensity of radiation may be used. Typical intensities of radiation that are conventionally employed in ophthalmologic practice may be adequate for the visualisation and photoactivation/uncaging requirements of the present invention.

Where a fluorescent marker is used in the system of the present invention, a predetermined wavelength and/or intensity of radiation (e.g. light) may be directed at the target site to confirm that the system is localised at the target site. Preferably, this predetermined wavelength and/or intensity of light is directed at the target site before the caged (e.g.photocaged) drug is activated. Any suitable wavelength of light may be used to cause luminescence. Suitable wavelengths range from 350 to 1000 nm, preferably 400 to 850 nm. The precise wavelengths used will depend on the nature of the marker. The activation may be achieved using a single photon or two/multi photon technique.

Preferably, the wavelength and/or intensity of light necessary to bring about luminescence is different to the wavelength of light required to activate the caged (e.g. photocaged) drug.

The present invention will now be described with reference to FIG. 1, which is a schematic diagram of an embodiment of the system of the present invention.

The system 10 comprises a photocaged drug 12 that is coupled to a magnetic nanoparticle 14 via a luminescent marker 16. The magnetic nanoparticle 14 comprises a magnetic core that is coated with a biocompatible coating to which biotin 18 is attached.

The luminescent marker 16 comprises a core formed from a quantum dot. The core is provided with an inner polymeric coating and an outer coating of streptavidin. The outer coating selectively adheres to the biotin coating 18 on the magnetic nanoparticle 14, conjugating the luminescent marker 16 to the magnetic nanoparticle 14.

The photocaged drug 12 comprises a therapeutic agent(R) that is coupled to a protective ligand or caging group by a photocleavable bond. The photocaged drug 12 is also provided with a biotin-carrying side-arm that selectively adheres to the streptavidin coating on the luminescent marker 16.

In use, the system 10 is administered to the patient parenterally. An external magnetic field is applied to the patient's eye to localise the system 10 at this target site. To ascertain whether the drug has been localised, a first wavelength of light is directed into the eye through its transparent media to activate the luminescent marker 16. Once activated, the marker 16 luminesces, providing the doctor with an indication of whether the system 10 is at its target location. The intensity of the luminescence may provide the doctor with an indication of whether an appropriate concentration of the system has reached the eye.

Once the system 10 is localised, a second wavelength of light is directed into the eye to activate the photocaged drug 12. This activation causes the therapeutic agent to be released at its target site. The second wavelength of light is different to the first wavelength of light, allowing activation of the marker 16 and photocaged drug 12 to be carried out in two separate steps.

The invention claimed is:

1. An ocular drug delivery system comprising:
   a photocaged drug comprising a therapeutic agent that is rendered biologically inactive by being coupled to a protective ligand or caging group by a photocleavable bond;
   wherein said therapeutic agent is capable of being activated and/or released in response to a predetermined wavelength and/or intensity of light which breaks said photocleavable bond;
   wherein said photocaged drug is coupled to a superparamagnetic nanoparticle; and
   wherein the system is suitable for delivering the drug to an eye; and
   wherein said therapeutic agent is capable of being activated and/or released in response to visible light having a wavelength from 400 nm to 1000 nm which breaks said photocleavable bond.

2. The system as claimed in claim 1 which further comprises a marker.

3. The system as claimed in claim 2 wherein the marker is luminescent.

4. The system as claimed in claim 1 wherein the superparamagnetic nanoparticle has a magnetic core that is 1 to 20 nm in size.

5. The system as claimed in claim 1 wherein the superparamagnetic nanoparticle has a size from 50 to 200 nm and a magnetic core.

6. The system as claimed in claim 4 wherein the superparamagnetic nanoparticle has a size from 50 to 200 nm.

7. The system as claimed in claim 5 wherein said therapeutic agent is capable of being activated and/or released in response to visible light having a wavelength from 400 nm to 800 nm which breaks said cleavable bond.

8. A method for drug delivery, said method comprising:
   administering the system as claimed in claim 1 to the patient, localising the system at the target site by the application of a magnetic field, and directing a predetermined wavelength and/or intensity of radiation to the target site to activate and release the caged drug at the target site.

9. The method as claimed in claim 8 wherein the system is administered parenterally to the patient.

* * * * *